United States Patent [19]
Ildstad et al.

[11] Patent Number: 6,039,684
[45] Date of Patent: Mar. 21, 2000

[54] NON-LETHAL CONDITIONING METHODS FOR THE TREATMENT OF ACQUIRED IMMUNODEFICIENCY SYNDROME

[75] Inventors: Suzanne T. Ildstad, Wynewood, Pa.; Olav B. Bergheim, Laguna Hills, Calif.

[73] Assignees: Allegheny University of the Health Sciences, Philadelphia, Pa.; Chimeric Therapies, Inc., Costa Mesa, Calif.

[21] Appl. No.: 08/988,832

[22] Filed: Dec. 11, 1997

[51] Int. Cl.⁷ .......................................................... A61N 5/00
[52] U.S. Cl. ................................................. 600/1; 128/898
[58] Field of Search ............................ 600/1–8; 128/897, 128/898

[56] References Cited

U.S. PATENT DOCUMENTS

| | | |
|---|---|---|
| 4,946,778 | 8/1990 | Ladner et al. . |
| 5,514,364 | 5/1996 | Ildstad . |
| 5,806,529 | 9/1998 | Reisner et al. ........................... 128/898 |

OTHER PUBLICATIONS

Rosenberg, "Total lymphoid versus total body irradiation for immunosuppressive therapy," Neurology, pp. 889–891, May 1987.

del Regato, "Trial of Fractionated Total–Body Irradiation in the Treatment of Patients with Acquired Immunodeficiency Syndrome: A Preliminary Report," American Journal of Clinical Oncology, p. 365, Aug. 1989.

Holland, "Allogeneic Bone Marrow Transplantation, Zidovudine, and Human Immunodeficiency Virus Type 1 (HIV–1) Infection," Annals of Internal Medicine, pp. 973–981, Dec. 1989.

Yatvin, "A multi–modality approach for the treatment of AIDS," Selective Cancer Therapeutics, pp. 23–28, Spring 1.

Klinman et al., "Effect of cyclophosphamide, total body irradiation, and zidovudine on retrovirus proliferation and disease progression in murine AIDS," AIDS Research and Human Retroviruses, pp. 101–106, Jan. 1992.

Giri et al., "Failure of allogeneic bone marrow transplantation to benefit HIV infection," Journal of Paediatric Child Health, pp. 331–333, Aug. 1992.

Shen et al., "Curative effect of split low dosage total–body irradiation on murine AIDS induced by Friend virus: the results and the possible mechanism," In Vivo, pp. 191–200, Mar. 1996.

Shen et al., "Murine AIDS cured by low dosage total body irradiation," Advances in Experimental Medicine and Biology, pp. 451–458, 1997.

Conill et al., 1997, "Radiation Therapy in AIDS–Related Cutaneous Kaposi's Sarcoma", Dermatol. 195:40–42.

Faure et al., "X Irradiation–Induced Transcription from the HIV Type 1 Long Terminal Repeat", AIDS Res. Human Retroviruses 11:41–43.

Fultz et al., 1995, "Effects of Total Lymphoid Irradiation on SIV–Infected Macaques", AIDS Res. Human Retroviruses 11:1517–1527.

Nakashima et al., 1986, "Quantitative Evaluations of the Effect of UV Irradiation on the Infectivity of HTLV–III (AIDS Virus) with HTLV–I–Carrying Cell Line, MT–4", J. Invest. Dermatol. 87:239–243.

Nobler et al., 1987, "The Impact of Palliative Irradiation on the Management of Patients with Acquired Immune Deficiency Syndrome", J. Clin. Oncol. 5:107–112.

Nobler, 1985, "Pulmonary Irradiation for Kaposi's Sarcoma in AIDS", Am. J. Clin. Oncol. 8:441–444.

Salai et al., 1997, "Human Immunodeficiency Virus (HIV) Inactivation of Banked Bone by Gamma Irradiation", J. Transplant. 2:55–56.

Shen et al., 1989, "Low Dose Total Body Irradiation: A Potent Anti–Retroviral Agent in vivo", Int. J. Radiation Oncol. Biol. Physiol. 16:165–170.

Smith et al., 1997, "Increased Cutaneous Toxicity to Ionizing Radiation in HIV–Positive Patients", Int. J. Dermatol. 36:779–782.

Vicenzi and Poli, 1994, "Ultraviolet Irradiation and Cytokines as Regulators of HIV Latency and Expression", Chemico–Biological Interactions 91:101–109.

Watkins et al., 1987, "Enhanced Mucosal Reactions in AIDS Patients Receiving Oropharyngeal Irradiation", Int. J. Radiation Oncol. Biol. Physiol. 13:1403–1408.

Xu et al., 1996, "Effect of Low–Dose Gamma radiation on HIV Replication in Human Peripheral Blood Mononuclear Cells", Photochem. Photobiol. 64:238–241.

Allan et al., 1995, "Infection of Baboons with Simian/Human Immunodeficiency Viruses", J. Acq. Imm. Deficien. Synd. Human Retro. 9:429.

Auchincloss & Sachs, 1975, "Mechanisms of Tolerance in Murine Radiation Bone Marrow Chimeras", Transpl. 36:436–441.

Carpenter et al., 1996, "Antiretroviral Therapy for HIV Infection in 1996", JAMA 276:146–154.

Cobbold et al., 1992, "Reprogramming the Immune System for Peripheral Tolerance with CD4 and CD8 Monoclonal Antibodies", Immunol. Rev. 129:165–201.

Cole et al., 1985, "The EBV–Hybridoma Technique and its Application to Human Lung Cancer", *Monoclonal Antibodies and Cancer Therapy*, Alan R. Liss, Inc. pp. 77–96.

(List continued on next page.)

*Primary Examiner*—Eric F. Winakur
*Attorney, Agent, or Firm*—Pennie & Edmonds LLP

[57] ABSTRACT

The present invention relates to the use of a non-lethal preparative regimen for the treatment of a patient with human immunodeficiency virus (HIV) disease. In a clinical trial, an HIV-positive patient was conditioned by non-lethal doses of irradiation and a chemotherapeutic drug prior to receiving donor bone marrow cells from a baboon. While long-term engraftment of donor cells was not observed, the non-lethal preparative conditioning regimen was able to reduce the viral burden and improved the clinical outcome. Such method is useful for treatment of patients with advanced acquired immunodeficiency syndrome (AIDS).

10 Claims, No Drawings

OTHER PUBLICATIONS

Cote et al., 1983, "Generation of human monoclonal antibodies reactive with cellular antigens", PNAS USA 80:2026–2030.

Dorshkind, 1990, "Regulation of Hemopoiesis by Bone Marrow Stromal Cells and Their Products", Annu. Rev. Immunol. 8:111.

Down et al., 1991, "Syngenetic Allogenetic Bone Marrow Engraftment After Total Body Irradiation: Dependence on Dose, Dose Rate, and Fractionation", Blood 77(3):661.

Greensberger, 1991, "The hematopoietic microenvironment", Crit. Rev. Oncology/Hematology 11:65–84.

Gupta et al., 1990, "A Semiquantitative Microassay for Measurement of Relative Number of Blood Mononuclear Cells Infected with Human Immunodeficiency Virus", Res. Human Restroviruses 6(10):1193–1193.

Heneine, 1996, "Highly Sensitive and Specific Polymerase Chain Reaction Assays for Detection of Baboon and Pig Cells Following Xenotransplantation in Humans", Transplan. 62:1360–1362.

Holland et al., 1989, "Allogenic Bone Marrow Transplantation, Zidovudine, and Human Immunodeficiency Virus Type 1 (HIV–1) Infection. Studies in a Patient with Non––Hodgkin Lymphoma", Ann. Int. Med. 111:973–981.

Kaufman et al., 1994, "Phenotypic Characterization of a Novel Bone Marrow–Derived Cell That Facilitates Engraftment of Allogeneic Bone Marrow Stem Cells", Blood 84:2436.

Kelleher et al., 1996, "Alterations in the Immune Response of Human Immunodeficiency Virus (HIV)–Infected Subjects Treated with an HIV–Specific Protease Inhibitor, Ritonavir", JID 173:321.

Kievits et al., 1991, "NASBA™ isothermal enzymatic in vitro nucleic acid amplification optimized for the diagnosis of HIV–1 infection", J. Virol. methods 35:273–286.

Koenig et al., 1995, "Transfer of HIV–1 specific cytotoxic T lymphocytes to an AIDS patient leads to selection for mutant HIV variants and subsequent disease progression", Nature Med. 1:330.

Kohler & Milstein, 1975, "Continuous cultures of fused cells secreting antibody of predefined specificity", Nature 256:495–497.

Kozbor et al., 1983, "The production of monoclonal antibodies from human lymphocytes", Immunology Tod. 4:72–79.

Lane, C.H. et al., 1990, "Syngeneic Bone Marrow Transplantation and Adoptive Transfer of Peripheral Blood Lymphocytes Combined with Zidovudine in Human Immunodeficiency Virus (HIV) Infection", Ann. Int. Med. 113(7):512–519.

Mayumi & Good, 1989, "Long–lasting Skin Allograft Tolerance in Adult Mice Induced Across Fully Allogeneic (Multimajor H–2 Plus Multiminor Histocompatibility) Antigen Barriers by a Tolerance–Inducing Method Using Cyclophosphamide", J. Exp. Med. 2:169–213.

McCarthy et al., 1985, "Characterization of Host Lymphoid Cells in Antibody–Facilitated Bone Marrow Chimeras", Transplantation 40(1):12–17.

McClure et al., 1987, "HIV infection of primate lymphocytes and conservation of the CD4 recpetor", Nature 330:487–489.

Michaels & Simmons, 1994, "Xenotransplant–Associated Zoonoses", Transplant. 57:1–7.

Monaco et al., 1966, "Studies on Heterologous Anti–lymphocyte Serum in Mice. III. Immunologic Tolerance and Chimerism Produced Across the H–2 Locus with Adult Thymectomy and Anti–Lymphocyte Serum", Ann. NY Acad. Sci. 129:190–209.

Morrison et al., 1984, "Chimeric human antibody molecules: Mouse antigen–binding domains with human constant region domains", PNAS USA 81:6851–6855.

Morrow et al., 1989, "Long–Term Observation of Baboons, Rhesus Monkeys, and Chimpanzees Inoculated with HIV and Given Periodic Immunosuppressive Treatment", AIDS Res. and Human Retro. 86:233–245.

Neuberger et al., 1984, "Recombinant antibodies possessing novel effector functions", Nature 312:604–608.

Pachl et al., 1995, "Rapid and Precise Quantification of HIV–1 RNA in Plasma Using a Branched DNA Signal Amplification Assay", J. AIDS 8:446–454.

Qin et al., 1990, "Induction of tolerance in peripheral T cells with monoclonal antibodies", Eur. J. Immunol. 20:2737–2745.

Riddell et al., 1996, "T–cell mediated rejection of gene–modified HIV–specific cytotoxic T lymphocytes in HIV–infected patients", Nature Med. 2:216–223.

Sharabi et al., 1990, "Specific Tolerance Induction Across a Xenogeneic Barrier Production of Mixed Rat/Mouse Lymphohematopoietic Chimeras Using a Nonlethal Preparative Regimen", J. Exp. Med. 172:195–202.

Sharabi & Sachs, 1989, "Mixed Chimerism and Permanent Specific Transplantation Tolerance Induced by a Nonlethal Preparative Regimen", J. Exp. Med. 169:493–502.

Slavin et al., 1978, "Transplantation Tolerance in Adult rats Using Total Lymphoid Irradiation: Permanent Survival of Skin, Heart, and Marrow Allografts", J. Exp. Med. 147(3):700–707.

Simmons & Torok–Storb, 1991, "Identification of Stromal Cell Precursors in Human Bone Marrow by a Novel Monoclonal Antibody, STRO–1", Blood 78:55–62.

Takeda et al., 1985, "Construction of chimaeric processed immunoglobulin genes containing mouse variable and human constant region sequences", Nature 314:452–454.

Vitetta & Uhr, 1985, "Immunotoxins", Ann. Rev. Immunol. 3:197–212.

Williams et al., 1987, "Diptheria toxin recpetor binding domain substitution with interleukin–2: genetic construction and properties of a diptheria toxin–related interleukin–2 fusion protein", Protein Engineering 1(6):493–498.

NON-LETHAL CONDITIONING METHODS FOR THE TREATMENT OF ACQUIRED IMMUNODEFICIENCY SYNDROME

1. INTRODUCTION

The present invention relates to the use of a non-lethal preparative regimen for the treatment of a patient with human immunodeficiency virus (HIV) disease. In a clinical trial, an HIV-positive patient was conditioned by non-lethal doses of irradiation and a chemotherapeutic drug prior to receiving donor bone marrow cells from a baboon. While long-term engraftment of donor cells was not observed, the non-lethal preparative conditioning regimen was able to reduce the viral burden and improved the clinical outcome. Such method is useful for treatment of patients with advanced acquired immunodeficiency syndrome (AIDS).

2. BACKGROUND OF THE INVENTION

2.1 BONE MARROW TRANSPLANTATION AND AIDS TREATMENT

Although combination antiretroviral therapy can dramatically suppress HIV replication for an extended period in some patients (Carpenter et al., 1996, JAMA 276:146), it alone does not restore immune function (Kelleher et al., 1996, JID 173:321). Several approaches to achieve immune reconstitution have been attempted, including allogeneic bone marrow transplantation and adoptive transfer of lymphocytes (Holland et al., 1989, Ann. Int. Med. 111:973; Lane et al., 1990, Ann. Int. Med. 113:512; Koenig et al., 1995, Nature Med. 1:330; Riddell et al., 1996, Nature Med. 2:216). However, these approaches have not been satisfactory because the transplanted cells are still susceptible to HIV infection. Therefore, cell-based therapy may require the development or isolation of HIV-1 resistant immune cells.

The search for an appropriate animal model for studying HIV infection has led to the recognition that most non-human primate species, including baboons, are naturally resistant to infection by HIV-1 (Morrow et al., 1989, AIDS Res. and Human Retro. 86:233; Allen et al., 1995, J Acq Imm Deficien. Synd. Human Retro. 9:429). Although baboon peripheral blood lymphoid cells are susceptible to non-productive infection with HIV-1 in vitro, repeated inoculations of HIV-1 in vivo failed to result in signs or symptoms of infection during more than three years of observation (McClure et al., 1987, Nature 330:487; Morrow et al. 1989). This suggested that the hematopoietic cells from a baboon donor may remain resistant to HIV-1 infection in a xenogeneic transplant environment, thereby potentially achieving immune reconstitution in an HIV-infected patient.

2.2 PREPARATIVE CONDITIONING REGIMENS FOR BONE MARRPW TRANSPLANTATION

The field of bone marrow transplantation was developed originally to treat bone marrow-derived cancers. It is believed by many that lethal conditioning of a human recipient is required to achieve successful engraftment of donor bone marrow cells in the recipient. Current conventional bone marrow transplantation has still primarily relied upon lethal conditioning approaches to achieve donor bone marrow engraftment. The requirement for lethal irradiation of the host which renders it totally immunocompetent poses a significant limitation to the potential clinical application of bone marrow transplantation to a variety of disease conditions, including solid organ or cellular transplantation, sickle cell anemia, thalassemia and aplastic anemia.

The risk inherent in tolerance-inducing conditioning approaches must be low when less toxic means of treating rejection are available or in cases of morbid, but relatively benign conditions. In addition to solid organ transplantation, hematologic disorders, including aplastic anemia, severe combined immunodeficiency (SCID) states, thalassemia, diabetes and other autoimmune disease states, sickle cell anemia, and some enzyme deficiency states, may all significantly benefit from a nonlethal preparative regimen which would allow partial engraftment of allogeneic or even xenogeneic bone marrow to create a mixed host/donor chimeric state with preservation of immunocompetence and resistance to GVHD. Moreover, the use of bone marrow from an HIV-resistant species offers a potential therapeutic strategy for the treatment of AIDS if bone marrow from a closely related species such as baboon also engrafts under similar nonlethal conditions, thereby producing new hematopoietic cells such as T cells which are resistant to infection by HIV.

A number of sublethal conditioning approaches in an attempt to achieve engraftment of allogeneic bone marrow stem cells with less aggressive cytoreduction have been reported in rodent models (Mayumi and Good, 1989, J Exp Med 169:213; Slavin et al., 1978, J Exp Med 147(3):700; McCarthy et al., 1985, Transplantation 40(1):12; Sharabi et al., 1990, J Exp Med 172(1):195; Monaco et al., 1966, Ann NY Acad Sci 129:190). However, reliable and stable donor cell engraftment as evidence of multilineage chimerism was not demonstrated, and long-term tolerance has remained a question in many of these models (Sharabi and Sachs, 1989, J. Exp. Med. 169:493; Cobbold et al., 1992, Immunol. Rev. 129:165; Qin et al., 1990, Eur. J. Immunol. 20:2737). Moreover, reproducible engraftment has not been achieved, especially when multimajor and multiminor antigenic disparities existed. More importantly, prior to the present invention, nonlethal or sublethal conditioning methods had not been contemplated as a therapeutic modality for HIV infection.

3. SUMMARY OF THE INVENTION

The present invention relates to non-lethal methods for the treatment of AIDS. In particular, it relates to the treatment of AIDS by non-lethal conditioning methods previously used as regimens for preparing recipients for bone marrow transplantation. Such methods include, but are not limited to, non-lethal doses of irradiation, host cell-specific antibodies, chemotherapeutic drugs or a combination thereof.

The invention is based, in part, on the Applicant's discovery that a patient with advanced HIV disease improved clinically after receiving a non-lethal dose of total lymphoid irradiation (TLI) and cyclophosphamide (CY) as conditioning regimen, followed by transplantation of baboon bone marrow donor cells. While the bone marrow transplantation did not produce long-term donor cell engraftment in the recipient, the disease condition of the patient improved significantly over time, as manifested by a reduction in viral burden. Although xenogeneic transplantation has not produced observable beneficial effects in the treated patient, the non-lethal conditioning methods are able to give rise to a clinically improved outcome. Therefore, a variety of uses are encompassed by the present invention described herein, including, but not limited to, the treatment of patients with advanced AIDS by the administration of a non-lethal dose of total body irradiation (TBI), a non-lethal dose of TLI, a host-cell-specific antibody or active fragments thereof such as anti-lymphocyte globulin (ALG), an alkylating agent such as CY, or a combination thereof.

4. DETAILED DESCRIPTION OF THE INVENTION

4.1 NON-LETHAL CONDITIONING METHODS

The efficacy and necessity of TBI in the facilitation of bone marrow engraftment have been demonstrated in a number of syngeneic and allogeneic models (Down et al., 1991, *Blood* 77(3):661). In earlier studies by Down et al, even syngeneic engraftment failed to occur in a murine model without some pretreatment of the recipient with TBI (Down et al., 1991, *Blood* 77(3):661). Minimal space and suppression were required for syngeneic reconstitution since partial engraftment occurred with as little as 2 Gy. However, significantly greater immunosuppression and/or "hematopoietic space" was required for MHC identical but minor antigen mismatched allogeneic marrow, resulting in failure of engraftment with less than 5.5 Gy of TBI (Down et al., 1991, *Blood* 77(3):661). The dose-response curve of engraftment versus radiation dose in these previous MHC-compatible studies was sigmoidal, with a steep increase in the percentage of allogeneic engraftment seen at doses of 6 Gy or greater.

For the purpose of the present invention, TBI may be administered in a modified manner in the form of TLI. TLI is delivered in the same fashion as TBI, except that the entire body of the recipient is not exposed. The irradiation is directed at lymphoid tissues such as the spleen, vertebral column, sternum, ribs, etc. As a result, TLI is, in essence, a partial TBI that is less aggressive and cyto-ablative, and thus higher doses may be administered without lethal effects. TLI conditioning may be supplemented by CY and/or ALG. These agents may be given before or after TLI. Preferably, they should be administered prior to TLI, and at one or more doses.

Historically, TLI has been utilized in fractionated doses to treat cancer patients. Typically, about 20 Gy is administered in approximately 10 divided doses at 2 Gy/dose. However, a single and relatively high (7.5–10 Gy) dose of TLI may also be used. The combined use of TLI, antibody and alkylating agent may further reduce the necessary dose of TLI.

4.1.1 ANTIBODY FOR USE IN CONDITIONING

In addition to the use of non-lethal doses of irradiation, antibodies may also be used in combination with it to further reduce the dose necessary for the treatment of AIDS. An example is ALG which has been used in certain conditioning regimens. The hematopoietic microenvironment is primarily composed of hematopoietic cells and stromal cells. The stromal cells occupy much space of the bone marrow environment and they include endothelial cells that line the sinusoids, fibroblastic cells such as adventitial reticular cells, perisinusoidal adventitial cells, periarterial adventitial cells, intersinusoidal reticular cells and adipocytes, and macrophages (Dorshkind, 1990, *Annu. Rev. Immunol.* 8:111; Greenberger, 1991, *Crit. Rev. Oncology/Hematology* 11:65). In addition, the Applicant has recently identified, characterized and purified a previously unknown cell type from the bone marrow that facilitates the engraftment of bone marrow stem cells across allogeneic and xenogeneic barriers. This cell referred to as hematopoietic facilitatory cell must be matched with the stem cell at the MHC for it to enhance stem cell engraftment. The facilitatory cells express a unique profile of cell surface markers: $Thy-1^+$, $CD3^+$, $CD8^+$, $CD45^+$ $CD45R^+$, MHC class $II^+$, $CD4^-$, $CD5^-$, $CD14^-$, $CD16^-$, $CD19^-$, $CD20^-$, $CD56^-$, $\gamma\delta$-$TCR^-$ and $\alpha\beta$-$TCR^-$. These cells are a newly recognized stromal cell population that is a critical component of the hematopoietic microenvironment. In allogeneic reconstitution experiments in mice, the murine facilitatory cells have been shown to be radiosensitive at about 3 Gy.

The various stromal cell types express a number of well-characterized surface markers, including but not limited to, vascular addressing, mannosyl and galactosyl residues, fasciculin III, villin, tetrapeptide, neural cell adhesion molecule receptor, hemonectin, B1 integrins, B2 integrins and B3 integrins (Greenberger, 1991, *Crit. Rev. Oncology/Hematology* 11:65). All the stromal cell populations including the facilitatory cells are potential targets of the conditioning regimen (U.S. Pat. No. 5,514,364), and thus, may also be the targets for AIDS treatment. Therefore, antibodies reactive with or specific for stromal cell surface markers may be used to deplete stromal elements in a cell type-specific non-lethal conditioning approach. For example, antibodies directed to Thy-1, MHC Class I and Class II molecules expressed on many stromal cell types may be used for this purpose. In addition, a monoclonal antibody designated STRO-1 has been shown to react with a cell surface antigen expressed by stromal elements in human bone marrow (Simmons and Torok-Storb, 1991, *Blood* 78:55). This antibody may be particularly useful for depleting stromal cells for making space in the bone marrow. In the mouse model, anti-Thy-1 and rabbit-anti-mouse-brain (RAMB) antibodies are effective in removing the facilitatory cell population from the bone marrow. RAMB is a polyclonal serum prepared by immunizing rabbits with homogenized mouse brain (Auchincloss and Sachs, 1983, *Transpl.* 36:436). Human brain also contains a number of epitopes cross-reactive with those expressed by the facilitatory cells. Thus, rabbit-anti-human-brain antibodies have been produced and may be used to remove the facilitatory cells from the hematopoietic microenvironment.

Also within the scope of the invention is the production of polyclonal and monoclonal antibodies which recognize novel antigens expressed by stromal cells including the facilitatory cells of the hematopoietic microenvironment for use as specific agents to deplete these cells.

Various procedures known in the art may be used for the production of polyclonal antibodies to antigens of stromal cells including facilitatory cells. For the production of antibodies, various host animals can be immunized by injection with purified or partially purified stromal cells including but not limited to rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody to antigens of stromal cells may be prepared by using any technique which provides for the production of antibody molecules by continuous cell lines in culture. These include but are not limited to the hybridoma technique originally described by Kohler and Milstein (1975, *Nature* 256: 495–497), and the more recent human B-cell hybridoma technique (Kosbor et al., 1983, *Immunology Today* 4:72; Cote et al., 1983, *Proc. Natl. Acad. Sci., USA* 80:2026–2030) and the EBV-hybridoma technique (Cole et al., 1985, *Monoclonal Antibodies and Cancer Therapy*, Alan R. Liss, Inc., pp. 77–96). Techniques developed for the production of "chimeric antibodies" by splicing the genes from a mouse antibody molecule of appropriate antigen specificity together with genes from a human antibody molecule can be used (e.g., Morrison et al., 1984, *Proc. Natl. Acad. Sci. USA*, 81:6851–6855; Neuberger et al., 1984, *Nature*, 312:604–608; Takeda et al., 1985, *Nature*

314:452–454). Such chimeric antibodies are particularly useful for in vivo administration into human patients to reduce the development of host anti-mouse response. In addition, techniques described for the production of single chain antibodies (U.S. Pat. No. 4,946,778) can also be adapted.

Antibody fragments which contain the binding site of the molecule may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments (*Antibody: A Laboratory Manual*, 1988, Harlow and Lane, Cold Spring Harbor).

4.2 USES OF ANTIBODIES TO STROMAL CELLS

A non-lethal conditioning method for the treatment of AIDS may be developed by totally eliminating the use of radiation or chemotherapeutic agents by using antibodies to deplete the critical targets of TBI. A likely target of such an approach is the various stromal cell populations that form the hematopoietic microenvironment. Antibodies directed to cell surface markers of stromal cells may be used to specifically deplete these cells which may harbor HIV. Alternatively, such antibodies may be used in conjunction with low doses of irradiation and/or cytotoxic drugs.

According to this embodiment, the antibodies of the present invention can be modified by the attachment of an antiproliferative or toxic agent so that the resulting molecule can be used to kill cells which express the corresponding antigen (Vitetta and Uhr, 1985, *Annu. Rev. Immunol.* 3:197–212). The antiproliferative agents which can be coupled to the antibodies of the present invention include but are not limited to agents listed in Table 1, infra, which is derived from Goodman and Gilman, 1990, *The Pharmacological Basis of Therapeutics*, Eighth Edition, Pergamon Press, New York, pp. 1205–1207, which is incorporated by reference herein.

Such antibody conjugates may be administered to an HIV-positive human patient. It is preferred that these conjugates are administered intravenously. Although the effective dosage for each antibody must be titrated individually, most antibodies may be used in the dose range of 0.1 mg/kg–20 mg/kg body weight. In cases where sub-lethal doses of irradiation are used, TLI of a human recipient may be administered at 5 to 10 Gy as a single dose or a combined total of 22 Gy administered in fractionated doses. Preferably, TLI may be used between 7.5–9.5 Gy. Alternatively, TBI may be administered between 5 Gy and 7 Gy.

TABLE 1

ANTI-PROLIFERATIVE AGENTS WHICH CAN BE COUPLED TO ANTIBODIES

| Class | Type | Agent |
|---|---|---|
| Alkylating Agents | Nitrogen Mustards | Mechlorethamine |
| | | Cyclophosphamide |
| | | Ifosfamide |
| | | Melphalan |
| | | Chlorambucil |
| | Ethylenimine Derivatives | Hexamethyl-melamine |
| | | Thiotepa |
| | Alkyl Sulfonates | Busulfan |
| | Nitrosoureas | Carmustine |
| | | Lomustine |
| | | Semustine |
| | | Streptozocin |

TABLE 1-continued

ANTI-PROLIFERATIVE AGENTS WHICH CAN BE COUPLED TO ANTIBODIES

| Class | Type | Agent |
|---|---|---|
| Antimetabolites | Triazenes | Dacarbazine |
| | Folic Acid Analogs | Methotrexate |
| | Pyrimidine Analogs | Fluorouracil |
| | | Floxuridine |
| | | Cytarabine |
| | Purine Analogs | Mercaptopurine |
| | | Thioguanine |
| | | Pentostatin |
| Natural Products | Vinca Alkaloids | Vinblastine |
| | | Vincristine |
| | Epipodophyllotoxins | Etoposide |
| | | Teniposide |
| | Antibiotics | Dactinomycin |
| | | Daunorubicin |
| | | Doxorubicin |
| | | Bleomycin |
| | | Plicamycin |
| | | Mitomycin |
| | Enzymes | L-Asparaginase |
| Miscellaneous Agents | Platinum Coordinated Complexes | Cisplatin Carboplatin |
| | Anthracenedione | Mitoxantrone |
| | Substituted Urea | Hydroxyurea |
| | Methyl Hydrazine Derivative | Procarbazine |
| | Adrenocortical Suppressant | Mitotane Aminoglutethimide |
| Hormones and Antagonists | Adrenocorticosteroids | Prednisone |
| | Progestins | Hydroxyprogesterone caproate |
| | | Medroprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| Radioactive Isotopes | Phosphorous | Sodium phosphate $^{32}$P |
| | Iodine | Sodium idoine $^{131}$I |
| Toxins | | Ricin A chain |
| | | Diphtheria toxin |
| | | Pseudomonas exotoxin A |

Any method known in the art can be used to couple the antibodies to an antiproliferative agent, including the generation of fusion proteins by recombinant DNA technology (Williams et al., 1987, *Protein Engineering* 1:493).

5. EXAMPLE: TREATMENT OF AIDS BY NONLETHAL CONDITIONING METHODS

5.1 MATERIALS AND METHODS

5.1.1 PATIENT SELECTION AND MEDICAL HISTORY

Major criteria for subject selection were: (1) documented infection with HIV-1, but not HIV-2; (2) advanced immunodeficiency, as determined by a total CD4$^+$ T cell count <75 cells/mm$^3$; (3) stable combination antiretroviral therapy (greater than two months); (4) greater than 50% cellularity on bone marrow biopsy; (5) clinically stable without evidence of an active or chronic opportunistic infection or malignancy; and (6) ability to give informed consent regarding the potential risks and benefits.

A 38 year old HIV-1 positive man was selected on the basis of the aforementioned criteria, and underwent a xenotransplant of baboon bone marrow after incomplete myeloablative conditioning on Dec. 14, 1995. The subject was first diagnosed to be HIV⁺ in 1985. His subsequent course has been notable for two episodes of *Pneumocystis carini* pneumonia (PCP) (December, 1992, September 1995), crytococcemia (January, 1993), wasting syndrome (March, 1994) and recurrent hospitalizations for bacterial pneumonia. His past medical history was otherwise significant for asthma, which developed after his first episode of PCP.

The subject consented for the study on day −21, where day 0 is the day of the transplant. At his initial baseline visit, his review of systems was notable for chronic disabling fatigue, weight loss, intermittent night fevers and sweats, bilateral peripheral neuropathy and chronic wheezing/dyspnea. His antiretroviral regimen included: indinavir 800 mg po tid (since August, 1995), lamivudine 150 mg po bid (since September, 1994) and zidovudine (AZT) 200 mg po tid (since 1990). Prior to the transplant, the subject had been on a stable antiretroviral regimen for 16 weeks. Other medications included acyclovir, itraconazole, recombinant growth hormone, and trimethoprim/sulfamethoxazole. His baseline physical examination was notable for a temporalis wasting, facial seborrhea, inspiratory and expiratory wheezing, diffuse muscle atrophy and bilateral sensory loss in the distal extremities.

At the day −14 the subject's zidovudine and growth hormone were discontinued. On days −3 and −2, the patient received 300 mg/m²/d (total dose: 1120 mg) of intravenous CY. On the morning of the transplant, the subject received 600 cGy of TLI, delivered first to the mantle field and then to a field incorporating the para-aortic lymph nodes, spleen, pelvic lymph nodes and inguinal nodes. Twelve hours later, baboon bone marrow enriched for CD34⁺ stem cells and progenitor facilitating cells was infused over 30 minutes via a subclavian line. Vancomycin (one gram every day) and cetazamide (one gram every eight hours) were given empirically post-transplant for 48 hours. On day +14, zidovudine and growth hormone were restarted. The subject remained hospitalized for observation until day +21, and has been monitored monthly since discharge. The subject has continued his regimen of indinavir, zidovudine and lamivudine during the post-transplant follow-up period (through nine months) except for two periods: (1) day +28 to +45, when zidovudine was stopped for an episode of neutropenia, and (2) day +180 to day +195 when all antiretroviral therapy was discontinued due to recurrent nephrolithiasis.

The treatment protocol was reviewed and approved by the Institutional Review Boards and Biosafety Committees at the University of California, San Francisco and the University of Pittsburgh. An Investigational New Drug application was approved by the Food and Drug Administration (FDA).

5.1.2 DONOR SELECTION AND BONE MARROW PROCESSING

Candidate donor baboons underwent screening for the presence of a variety of infectious agents, using a modified protocol developed at the University of Pittsburgh (Michaels and Simmons, 1994, Transplant. 57:1–7). Each animal underwent serological testing for: Epstein Barr Virus (EBV), foamy virus, simian agent 8 (analogs to human HSV), cytomegalovirus (CMV), STLV, SRV, SIV, HIV-1, HIV-2, Herpes B, HTLV, Monkey Pox, SHFV, Baboon SA12, Filovirus, hepatitis A, B and C, *Toxoplasmosis gondi*. Prior exposure to *Mycobacterium tuberculosis* was evaluated by skin testing. All assays were performed at least twice. Prior to transplantation, the baboon donor was transferred to the University of Pittsburgh, where it was placed in isolation. Bone marrow was obtained from the baboon, and enriched for the facilitating cell and stem cell populations.

Briefly, bone marrow was harvested and transported to San Francisco. A Baxter ferromagnetic device was used to remove mature lymphoid lineages, using a modified technique previously described (Kaufman et al., 1994, Blood 84:2436). Adequacy of cellular depletions as well as cellular viability was performed immediately following processing using flow cytometric analysis. Quality control testing included: (1) colony assays, (2) sterility culture pre- and post-treatment, and (3) flow cytometric analysis for all known lineages, including stem cells, progenitor cells and facilitating cells.

5.1.3 TRANSPLANT PROCEDURE AND POST-TRANSPLANT MONITORING

Prior to the transplant, the subject underwent partially myeloablative conditioning using TLI and CY. On days −3 and −2 (where day 0 was the day of the transplant), the subject received intravenous CY (300 mg/m²/d). On day 0, the subject received 600 cGy of non-fractionated TLI. Twelve hours later, 3.32×10⁶ CD34⁺ cells/kg recipient weight and 1.2×10⁶ facilitating cells/kg recipient weight were infused over 30 minutes via a subclavian central line. The patient was hospitalized for observation for 21 days in the General Clinical Research Center (GCRC) at San Francisco General Hospital.

All concurrent therapies, including prophylaxis for *Pneumocystis carini*, were continued. The subject's antiretroviral regimen was continued during the study period, with the exception of AZT, which was discontinued from day −14 to day +14 to avoid myelosuppression. The subject's recombinant growth hormone, an experimental therapy for AIDS wasting syndrome, was also discontinued from day −14 to day +14. Intravenous foscarnet was administered as CMV prophylaxis from day −2 to day +21. GVHD prophylaxis was not used.

The subject was evaluated three times pre-transplant (days −14, −7, −3), daily as an inpatient (days 0 to +21), weekly for the first four weeks post-discharge (days +28, +35, +42, and +49), and then monthly. At each visit, a physical examination was performed, and safety laboratory data obtained (including hematological and metabolic tests). At multiple time-points the subject had the following assays performed: T cell subsets (CD4, CD8), HIV-1 RNA (bDNA, NASBA), peripheral blood mononuclear cell (PBMC) co-culture and mixed lymphocyte reaction (MLR). Samples were also obtained and analyzed for the presence of baboon-derived viral infection.

5.1.4 ENUMERATION OF LINEAGE PRODUCTION

Flow cytometric analysis for engraftment was carried out using several techniques. Pre- and post-transplant, the patient's PBMC were analyzed by staining for mature lineage markers known to cross react on baboon lineages versus markers known to be specific for human but not baboon markers. A class I-specific monoclonal antibody (moAb) specific for the recipient which did not cross react on the donor cells was available, however, the reverse was not. Therefore, cells of baboon origin could only be detected by negative staining. While this protocol could easily detect populations present at 5% of total cells, this procedure was not appropriate to detect rare events. During the post transplant course, cells of baboon origin were not detected at any time by flow cytometry, suggesting that the presence of baboon cells at days 5 and 14 were less than 5% of total hematopoietic lineages.

Whole blood preserved with ACD was sent to the Retrovirus Diseases Branch, Centers for Disease Control and Prevention, Atlanta, Ga., for analysis using a specific and sensitive assay for detecting baboon cells in an xenotransplant environment (Heneine, 1996). Briefly, a polymerase chain reaction (PCR) based assay using a primer directed at a baboon specific mitochondrial sequence was used to analyze the DNA lysates obtained from the baboon recipient.

5.1.5 FLOW CYTOMERY

Determination of lymphocyte subsets were performed using standard flow cytometric analysis of whole blood preserved with ACD. Approximately 10 μl of blood was stained with appropriate concentrations of directly conjugated (PE, FITC or PerCP) antibodies against the following markers: CD4 (SK3: Becton Dickinson, San Jose, Calif.), CD8 (SK1:Becton Dickinson), CD3 (SK7:Becton Dickinson), αβ TCR (BMA-031:T Cell Diagnostics, Hialeah, Fla.), CD16(NK15:Becton Dickinson), CD19 (4G7:Becton Dickinson), CD20(L27:Becton Dickinson), CD33 (P676:Becton Dickinson), CD45 (2D1:Becton Dickinson), CD56 (MY31:Becton Dickinson), HLA Class I (MCA81F:Serotec), HLA-DR (L243:Becton Dickinson). The antibody/cell mixture was incubated in the dark for 30 minutes at 4 degrees C. The cells were treated with 2 ml of FACSLyse (Becton-Dickinson) for 6–10 minutes at room temperature, and then centrifuged for 5 minutes at 1100 rpm. The supernatant was aspirated and then the tubes were washed again with 2 ml of PBS containing 2% bovine serum albumin and 1% azide. The pellet was then resuspended in 2% paraformaldehyde, and tubes were kept overnight before analysis on a Becton Dickinson FACScan on FACS Calibur.

5.1.6 MIXED LYMPHOCKYTE REACTION

MLR assays were performed on peripheral blood samples collected in ACD tubes which were shipped overnight from San Francisco to Pittsburgh. The peripheral blood was diluted 1:4 with HBBS without $CA^{++}$ or $Mg^{++}$ (Gibco, Grand Island, N.Y.) and underlayered with Ficol-Hypaque (Pharmacia, Piscataway, N.J.) in 50 ml conical tubes (Costar, Cambridge, Mass.). The tubes were centrifuged at 22 degrees C. for 30 minutes at 1200 rpm. The resulting buffy coat was aspirated, and washed twice in HBBS without ions for 10 minutes at 1200 rpm. Cells were counted and resuspended in plating media (RPMI-1640; Gibco) containing 4 mM Hepes buffer (Gibco), 50 μg/ml gentamycin sulfate (Gibco), and 5% heat inactivated human serum (C-six), at a concentration of $1 \times 10^6$/ml. Responding and stimulating populations were plated at a density of $1 \times 10^5$ cells/well each in a total volume of 200 μl in 96 well plates. The plates were incubated with 1 μCi irradiated thymidine/well, and incubated for an additional 18 to 24 hours. The plates were harvested on day 6 on a Skatron harvester, and $^3$H thymidine uptake was measured on a Wallace Beta Plate counter. Non-specific proliferation was measured by 48 hour incubation of triplicate wells to 50 μg/ml of phytohemagglutinin (PHA, Gibco), followed by labeling wells with $^3$H-thymidine, and harvesting these wells at 72 hours. A positive result was considered to be a count three times greater than the background proliferation.

5.1.7 CYTOTOXIC ASSAYS

To assess cytotoxicity, peripheral blood lymphocytes were isolated as described above, and resuspended in $1 \times 10^6$ cells/ml in plating media. Target cells (either fresh PBL or thawed splenocytes) were cultured in plating media containing PHA (50 μg/ml) for 72 hours. Activated blasts were then spun down and the cell pellet was incubated with 20 μCi of $^{51}$Cr at 37° C. after 90 minutes in a humidified $CO_2$ atmosphere. The plates were then harvested and supernatants measured for chromium release on a gamma counter. A positive result was considered to be greater than 10% using the following formula: Percent Kill=(Experimental CPM−Background CPM×100)/(Total CPM−Background CPM).

5.1.8 QUANTITATIVE PLASMA HIV-1 RNA

Plasma HIV-1 RNA levels were monitored using two commercially available assays: branched DNA (bDNA) and Nucleic Acid Sequence Based Amplification (NASBA). After sampling, plasma was separated by centrifugation, and stored at −80 degrees Celsius. Batched samples were analyzed using a quantitative bDNA signal amplification assay as described elsewhere (Pachl et al., 1995, J. AIDS 8:446). Plasma samples were also analyzed with regard to HIV-1 RNA levels using the NASBA assay (Kievits et al., 1991, J. Virol. Methods 35:273).

5.1.9 QUANTITATIVE HIV-1 CULTURE

Quantitative HIV-1 culture was performed as described by Gupta et al (1990) with further modification developed by the AIDS Clinical Trials Group (ACTG). Briefly, six serial five-fold dilutions of PBMC from the subject was cocultured in duplicate with $1 \times 10^6$ PHA-stimulated normal donor PBMC in 2 ml of RPMI 1640 medium containing 20% fetal calf serum and 5% natural IL-2 (Cellular Products, Buffalo, N.Y.). Every seven days, half of the medium was removed and replaced with the same volume of medium containing $0.5 \times 10^6$ PHA-stimulated normal donor PBMC. The cultures were maintained for a total of 21 days. Culture fluids were tested at day 21 for the presence of HIV-1 p24 by the antigen capture test (Dupont, Wilmington, Del.). A culture was considered positive for HIV when 30 pg or more of HIV p24 was detected in the supernatant of either of the duplicate wells. The minimum number of patient's PBMC showing a positive virus culture was considered the end point. Results were expressed as the number of virus-producing cells per million PBMC.

5.1.10 QUANTITATIVE DNA PCR

The level of proviral DNA in PBMC was performed by an internally controlled PCR (ICPCR) assay. Briefly, duplicate cell lysates from $1.25 \times 10^5$ PBMC (equivalent to 1 μg of DNA measured by cell count) were mixed with 500 copies of a plasmid HIV-1 gag DNA carrying a 45-bp deletion in the target sequence and then coamplified with gag primers 101/145 under conditions described previously (ref). A one-third volume of the 100 μl amplification reaction product was hybridized in solution to the $^{32}$P-labeled oligonucleotide probe 102 (250,000 to 300,000 cpm per sample). The oligonucleotide probe-target DNA heteroduplex was resolved by electrophoresis in a 10% polyacrylamide gel. The gel was dried and the signal intensity of the amplifiers derived from the samples and from the exogenously added deletion plasmid DNA standard was measured with a phosphorimager. The amount of HIV-1 DNA in the sample was quantitated by interpolation from a standard curve generated for each experiment with known copies of deletion plasmid DNA by serial 10-fold dilutions of stock plasmid DNA of known concentration.

5.1.11 INFECTION OF BABOON AND HUMAN PBMC WITH HIV-1

Baboon and human PBMC were infected with HIV-1 from the subject. Briefly, $7 \times 10^6$ cells were incubated with PHA-P (5 μg/ml) for 3 days and then infected for one hour with 1 ml ($1 \times 10^5$ pg of p24) of cell-free HIV-1 isolated during pre- and post-transplantation. Cells were washed 3 times and cultured for 21 days in RPMI 1640 medium containing 5% IL-2 and 20% FCS. Culture fluids were tested at indicated days for the presence of HIV-1 p24 by the antigen capture test (Dupont). During the culture period $0.5 \times 10^6$ cells were also harvested at days 0, 12 and 21, and stored at −70° C. in a pellet from qualitative DNA PCR.

5.1.12 QUALITATIVE DNA PCR

Qualitative DNA PCR was performed on lyzed cells without purification of DNA. Amplification was carried out by the gag-specific prier SK101/145 and the amplifier was detected by liquid hybridization with a $^{32}$P-labeled internally conserved sequence probe 102 followed by polyacrylamide gel electrophoresis. The characteristic fragment of defined size was visualized with the signal intensity was quantitated in the phosphorimager.

5.2 RESULTS

Thirty baboons were screened for various infectious agents. The selected donor was a 62 kg adult male, bred in the United States of research purposes. Serological tests were negative for foamy virus, SA8 and CMV, all three of which were common in adult baboons. However, the donor had evidence for prior infection with simian EBV. All other screening tests were negative.

The bone marrow infusion resulted in a transient episode of hypotension, which resolved after reducing the infusion rate. The combination of CY (600 mg/m$^2$ total) and TLI (600 cGy) was well tolerated. The subject experienced mild to moderate nausea during days +3 to +7, which was judged to be secondary to radiation-induced enteritis.

Immediately after the conditioning regimen, there was an immediate and profound decrease in the absolute lymphocyte count (ALC), falling from a mean baseline of 2700 cells/mm to 300 cells/mm day +1. The ALC remained low through day +21, then slowly increased to approximately 1500 to 2000, significantly below the subject's baseline. Levels of neutrophils, platelets and red blood cells declined over the immediate 2 to 4 week post-transplant period, returning to baseline levels by month two. There were no significant hepatic or metabolic abnormalities associated with the transplant or conditioning regimens. All safety parameters returned toward baseline by month two.

During the nine months of follow-up, the subject has remained clinically stable. He has not developed a new AIDS defining opportunistic infection or any HIV-related complications (except an episode of nephrolithiasis thought to be secondary to indinavir). During the immediate post-transplant period, the subject reported subjective improvement in several chronic symptoms, including chronic fatigue, recurrent sinusitis, recurrent asthma exacerbations, night sweats and severe facial seborrhea. His weight has also increased since the pre-transplant period. The patient reported the return of a sense of smell and taste. It should be noted that the patient did not report any subjective benefit from the use of aggressive three drug antiretroviral therapy (AZT, lamivudine, indinavir) during the four months of treatment prior to the transplant.

Phenotypic studies, using flow cytometric analysis, did not show evidence of baboon cells in the peripheral blood of the patient through month 6 post-transplant. Since no cells of baboon origin were detected at any time by flow cytometry, this indicates that the baboon cells detected at days 5 and 14 were present at less than 5% of total hematopoietic lineages.

PCR studies (lower limit of detection of less than 0.001%) also did not show any evidence of baboon cells in the periphery. However, PCR analysis using primers directed against baboon mitochondrial DNA showed evidence of donor cells on days 5 and 13, but not subsequently.

The subject's mean baseline CD4$^+$ T lymphocyte count was 45 cells/mm$^3$. Post-transplant, the level decreased significantly (to less than 10 cells/mm$^3$), slowly returning to baseline by month two. Total CD8$^+$ T lymphocyte counts followed a similar trend, dropping from a mean baseline of 1530 cells/mm$^3$ to less than 500 cells/mm$^3$ during the post-transplant period. In general, the absolute number of CD4$^+$ and CD8$^+$ T cells paralleled changes in the ALC.

The absolute numbers of B-cell (CD19$^+$) also dropped dramatically after the conditioning, and gradually increased during the 9 months post-transplant. Natural killer (NK) cells similarly declined post-transplant, and remained low through day 28. NK cells returned to baseline during the second month post-transplant (notably, the patient received subcutaneous G-CSF for neutropenia just prior to the increase in NK cell levels).

Peripheral blood was obtained from the patient two weeks prior to transplant. The cells were tested for reactivity in both MLR and CML. Positive MLR responses were found to PHA, third party allogeneic stimulators, and to the donor baboon prior to transplant. In CML assays, the isolated cells showed killing of both allogeneic and xenogeneic targets. Approximately one month after the transplant, MLR results showed pan-hyporeactivity against the donor, third party allogeneic targets, and a much lower albeit still positive response to PHA (4 times background). At seven weeks post transplant, the patient's cells showed a strong response to PHA, a response to allogeneic stimulators, and were unreactive to stimulators from either the donor baboon or a third party xenogeneic stimulator. All stimulator cells induced responses from control allogeneic responders.

However, repeated MLR assays at 4 months after the transplant showed poor PHA responses. Interestingly, allogeneic and xenogeneic reactivity (also against the donor baboon) were present in spite of a low PHA response. A similar pattern was noted for MLR assays at 6 months post-transplant. In spite of a poor PHA response, the patient's cells mounted a proliferative response to both allogeneic and donor xenogeneic stimulators. At eight months post-transplant, the PHA response returned. At this time, the patient's cells responded to allogeneic stimulators, but not to donor or third party xenogeneic antigens, as seen at one month post-transplant. The patient's cells did not proliferate in response to influenza and tetanus antigens.

Plasma viral load was monitored pre- and post-transplant using assays for plasma HIV-1 RNA (bDNA, NASBA), proviral DNA and viral culture. Plasma HIV-1 RNA levels (using a bDNA assay) had mean pre-transplant level of 57,000 copies/mm$^3$. At day +4, the levels declined significantly to 2100 copies/mm$^3$. The HIV-1 RNA levels remained low through 6 months of follow-up, increasing transiently at days +14 and day +35. Similar trends were seen using the NASBA assay, with a similar transient increase at day +14 and day +35.

Cell-associated infectious HIV-1 titer also decreased significantly (approximately 25-fold) during the six months of post-transplant follow-up, with a transient increase noted at day 19. The level of proviral DNA in PBMC as detected by the quantitative PCR decreased approximately 3-fold during six months of follow-up.

Baboon PBMC were previously shown to be resistant to replication of HIV-1 IIIB, a laboratory strain of HIV-1. To determine whether baboon PBMC still maintained this property, viral DNA synthesis was measured by qualitative DNA PCR following infection. No significant HIV-1 DNA PCR signal was observed in baboon PBMC up to 21 days post-infection.

The possibility existed that the patient's own PBMC after transplantation of baboon bone marrow cells became resistant to HIV-1 infection by some cytokines released from the baboon cells. In that connection, 5×10$^6$ human PBMC were cocultivated with equal number of baboon PBMC in the presence of PHA for 4 days. As a control, human PBMC were stimulated alone in the presence of PHA for the same length of time. Following stimulation, cells were infected with HIV-1 obtained three days before transplantation. Again, no difference in viral growth was observed between cocultivated PBMC and control human PBMC. Therefore, it is concluded that the improvement of disease condition in the treated patient was produced by the non-lethal conditioning methods that were originally intended for use in preparing the patient for receiving donor bone marrow cells.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description. Such modifications are intended to fall within the scope of the appended claims.

All publications cited herein are incorporated by reference in their entirety.

What is claimed is:

1. A method for reducing HIV viral burden comprising:
    selecting an HIV-infected human subject having acquired immunodeficiency syndrome, and
    administering to the subject a non-lethal dose of irradiation to reduce HIV viral burden in the subject.

2. The method of claim 1 in which the irradiation is total body irradiation.

3. The method of claim 2 in which the dose of total body irradiation is between 1 and 7 Gy.

4. The method of claim 1 in which the irradiation is total lymphoid irradiation.

5. The method of claim 4 in which the dose of total lymphoid irradiation is between 5 and 10 Gy.

6. The method of claim 1 which further comprises administering an alkylating agent to the subject.

7. The method of claim 6 in which the alkylating agent is cyclophosphamide.

8. The method of claim 1 which further comprises administering an antibody or an active fragment thereof to the subject.

9. The method of claim 8 in which the antibody is anti-lymphocyte globulin.

10. The method of claim 8 in which the antibody is a monoclonal antibody.

* * * * *